United States Patent
Wolters et al.

(10) Patent No.: US 8,134,698 B1
(45) Date of Patent: Mar. 13, 2012

(54) DYNAMIC RANGE EXTENSION IN SURFACE INSPECTION SYSTEMS

(75) Inventors: Christian Wolters, Cambell, CA (US); Anatoly Romanovsky, Palo Alto, CA (US); Daniel Kavaldjiev, Milpitas, CA (US); Bret Whiteside, Gilroy, CA (US)

(73) Assignee: KLA-Tencor Corporation, Milpitas, CA (US)

(*) Notice: Subject to any disclaimer, the term of this patent is extended or adjusted under 35 U.S.C. 154(b) by 1034 days.

(21) Appl. No.: 12/049,091

(22) Filed: Mar. 14, 2008

(51) Int. Cl.
*G01N 21/00* (2006.01)

(52) U.S. Cl. .................. 356/237.1; 356/237.2

(58) Field of Classification Search ..... 356/237.1–237.5
See application file for complete search history.

(56) References Cited

U.S. PATENT DOCUMENTS

| | | |
|---|---|---|
| 6,201,601 B1 | 3/2001 | Vaez-Iravani et al. |
| 6,271,916 B1 | 8/2001 | Marxer et al. |
| 6,313,467 B1 | 11/2001 | Shafer et al. |
| 6,538,730 B2 | 3/2003 | Vaez-Iravani et al. |
| 6,597,000 B2 | 7/2003 | Stern |
| 6,618,134 B2 | 9/2003 | Vaez-Iravani et al. |
| 6,657,714 B2 | 12/2003 | Almogy et al. |
| 6,914,670 B1 | 7/2005 | Almogy et al. |
| 7,304,310 B1 | 12/2007 | Shortt |
| 2002/0054291 A1 | 5/2002 | Tsai et al. |
| 2002/0093648 A1 | 7/2002 | Nikoonahad et al. |
| 2002/0105636 A1 | 8/2002 | Okawauchi |
| 2002/0109110 A1 | 8/2002 | Some et al. |
| 2003/0058433 A1 | 3/2003 | Almogy et al. |
| 2005/0073686 A1 | 4/2005 | Roth et al. |
| 2006/0007435 A1* | 1/2006 | Biellak et al. ............. 356/237.3 |
| 2007/0013898 A1 | 1/2007 | Wolters et al. |
| 2008/0013084 A1* | 1/2008 | Matsui et al. ............. 356/237.5 |

* cited by examiner

Primary Examiner — Michael P Stafira
(74) Attorney, Agent, or Firm — Luedeka Neely Group, P.C.

(57) ABSTRACT

In one embodiment, a surface analyzer system comprises a radiation targeting assembly to target a radiation beam onto a surface; and a scattered radiation collecting assembly that collects radiation scattered from the surface. The radiation targeting assembly generates primary and secondary beams. Data collected from the reflections of the primary and secondary beams may be used in a dynamic range extension routine, alone or in combination with a power attenuation routine.

26 Claims, 7 Drawing Sheets

DYNAMIC RANGE EXTENSION IN SURFACE INSPECTION SYSTEMS

RELATED APPLICATIONS

None

BACKGROUND

The subject matter described herein relates to surface inspection techniques, and more particularly to dynamic range extension in surface inspection systems.

Semiconductor materials may be inspected for defects such as, e.g., surface imperfections, particles, irregularities in the thickness of thin film coatings, and the like, which may hamper the performance of the semiconductor material. Some existing inspection systems direct a beam of radiation on the surface of the semiconductor material, then collect and analyze light reflected and/or scattered from the surface to quantify characteristics of the surface. Additional inspection techniques are desirable. In particular, it is desirable to inspect the edge or near edge of semiconductor wafers, compound semiconductor wafers, transparent wafers or thin film disks for defects.

BRIEF DESCRIPTION OF THE DRAWINGS

The detailed description is described with reference to the accompanying figures.

DETAILED DESCRIPTION

Figure 1:
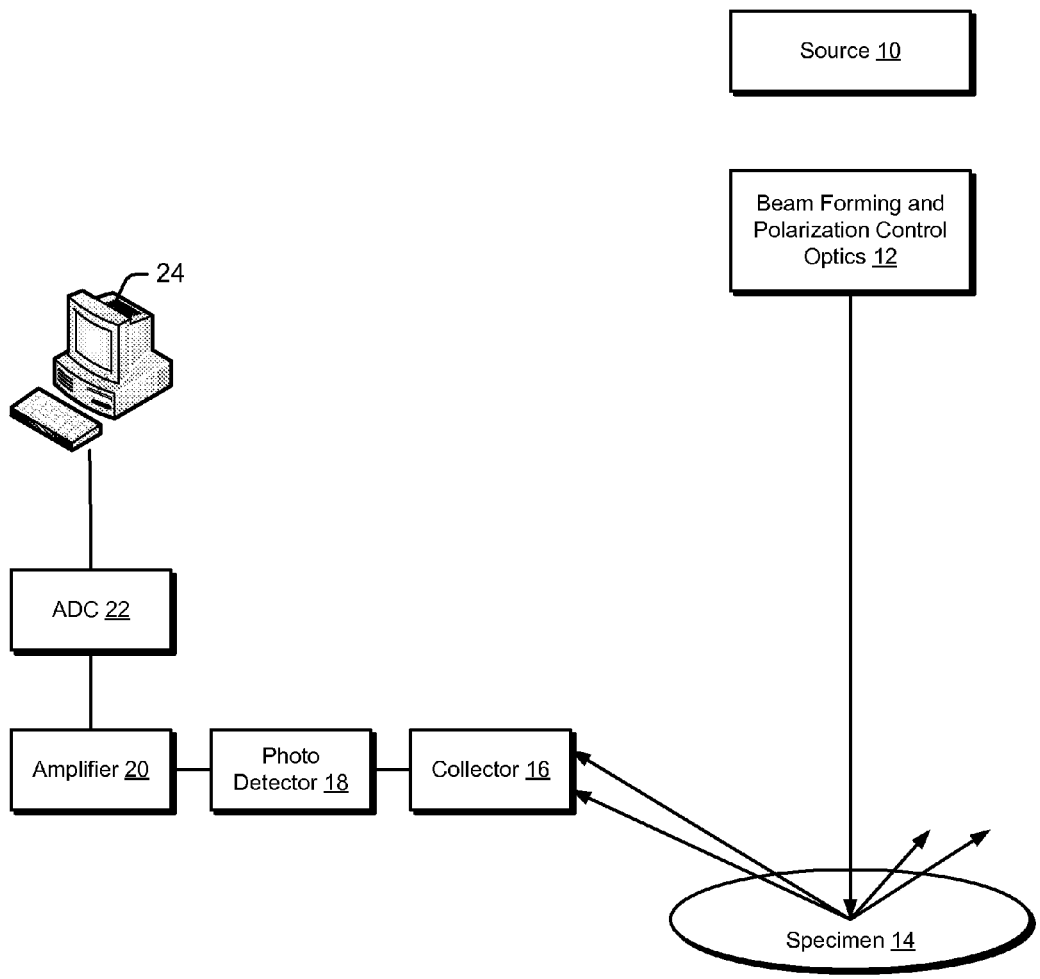
FIG. 1 is a schematic illustration of various components of a surface inspection system, according to embodiments.

Described herein are exemplary systems and methods for dynamic range extension in surface inspection systems. In the following description, numerous specific details are set forth in order to provide a thorough understanding of various embodiments. However, it will be understood by those skilled in the art that the various embodiments may be practiced without the specific details. In other instances, well-known methods, procedures, components, and circuits have not been described in detail so as not to obscure the particular embodiments.

Various methods described herein may be embodied as logic instructions on a computer-readable medium. When executed on a processor the logic instructions cause a processor to be programmed as a special-purpose machine that implements the described methods. The processor, when configured by the logic instructions to execute the methods described herein, constitutes structure for performing the described methods.

The methods and systems described herein enhance defect detection by addressing various limiting factors of measurement detection range including, but not limited to, detector saturation, amplifier saturation and the fixed bit range of analog-to-digital converters (ADC). Unlike some currently used inspection methods, the inspection system described herein is able to extend the measurement detection range while maintaining signal linearity and stability, and without employing additional detectors, optics and electronic components, all of which undesirably increase space consumption, complexity and cost of the inspection system.

Various embodiments are described herein for an optical inspection system or tool that may be used for inspecting a specimen. The term "specimen" is used herein to refer to a wafer, a reticle, or any other sample that may be inspected for defects, features, or other information (e.g., an amount of haze or film properties) known in the art.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

In some cases, a wafer may include only the substrate, such as a virgin wafer. Alternatively, a wafer may include one or more layers that may be formed upon a substrate. Examples of such layers may include, but are not limited to, a resist, a dielectric material, and a conductive material. A resist may include a resist that may be patterned by an optical lithography technique, an e-beam lithography technique, or an X-ray lithography technique. Examples of a dielectric material may include, but are not limited to, silicon dioxide, silicon nitride, silicon oxynitride, and titanium nitride. Additional examples of a dielectric material include "low-k" dielectric materials such as Black Diamond™ which is commercially available from Applied Materials, Inc., Santa Clara, Calif., and CORAL™ commercially available from Novellus Systems, Inc., San Jose, Calif., "ultra-low k" dielectric materials, such as "xerogels," and "high-k" dielectric materials, such as tantalum pentoxide. In addition, examples of conductive materials may include, but are not limited to, aluminum, polysilicon, and copper.

One or more layers formed on a wafer may be "patterned" or "unpatterned." For example, a wafer may include a plurality of dies having repeatable pattern features. Formation and processing of such layers of material may ultimately result in completed semiconductor devices. As such, a wafer may include a substrate on which not all layers of a complete semiconductor device have been formed, or a substrate on which all layers of a complete semiconductor device have been formed. The term "semiconductor device" may be used interchangeably herein with the term "integrated circuit." In addition, other devices such as microelectromechanical (MEMS) devices and the like may also be formed on a wafer.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as quartz. A reticle may be disposed above a resist-covered wafer during an exposure step of a lithography process such that the pattern on the reticle may be transferred to the resist. For example, substantially opaque regions of the reticle may protect underlying regions of the resist from exposure to an energy source.

FIG. 1 is a schematic illustration of various components of a surface inspection system, according to embodiments. The system shown in FIG. 1 illustrates a general optical configuration that can be used to inspect a specimen according to the methods described herein. The inspection system includes a dark-field optical subsystem. It will be obvious to one of ordinary skill in the art that the illustrated system may be altered in many ways while still providing the capability to perform the methods described herein. In addition, it will be obvious to one of ordinary skill in the art that the illustrated system may include various additional components that are not shown in FIG. 1 such as a stage, a specimen handler, folding mirrors, polarizers, additional light sources, additional collectors, etc. All such variations are within the scope of the invention described 10 herein.

The system illustrated in FIG. 1 includes an illumination subsystem. The illumination subsystem is configured to direct light to a specimen. For example, the illumination subsystem includes light source 10. Light source 10 may include, for example, a laser, a diode laser, a helium neon laser, an argon laser, a solid state laser, a diode pumped solid state (DPSS) laser, a xenon arc lamp, a gas discharging lamp, or an incandescent lamp. The light source may be configured to emit near monochromatic light or broadband light. In general, the illumination subsystem is configured to direct light having a relatively narrow wavelength band to the specimen (e.g., nearly monochromatic light or light having a wavelength range of less than about 20 nm, less than about 10 nm, less than about 5 nm, or even less than about 2 nm). Therefore, if the light source is a broadband light source, the illumination subsystem may also include one or more spectral filters that may limit the wavelength of the light directed to the specimen. The one or more spectral filters may be bandpass filters and/or edge filters and/or notch filters.

The illumination subsystem also includes various beam forming and polarization control optics 12. For example, the illumination subsystem may include various optics for directing and supplying an incident beam to specimen 14 with, e.g., a particular spot size. If the light source is configured to emit light of various polarizations, the illumination subsystem may also include one or more polarizing components that may alter the polarization characteristics of the light emitted by the light source. In some cases, the light directed to specimen 14 may be coherent or incoherent. The beam forming and polarization control optics 12 may include a number of components, which are not shown in FIG. 1, such as a beam expander, folding mirrors, focusing lenses, cylindrical lenses, beam splitters, etc.

In some cases, the illumination subsystem may include a deflector (not shown). In one embodiment, the deflector may be an acousto-optical deflector (AOD). In other embodiments, the deflector may include a mechanical scanning assembly, an electronic scanner, a rotating mirror, a polygon based scanner, a resonant scanner, a piezoelectric scanner, a galvo mirror, or a galvanometer. The deflector scans the light beam over the specimen. In some embodiments, the deflector may scan the light beam over the specimen at an approximately constant scanning speed.

As shown in FIG. 1, the illumination subsystem may be configured to direct the beam of light to the specimen at a normal angle of incidence. In this embodiment, the illumination subsystem may not include a deflector since the normal incidence beam of light may be scanned over the specimen by relative motion of the optics with respect to the specimen and/or by relative motion of the specimen with respect to the optics. Alternatively, the illumination subsystem may be configured to direct the beam of light to the specimen at an oblique angle of incidence. The system may also be configured to direct multiple beams of light to the specimen such as an oblique incidence beam of light and a normal incidence beam of light. The multiple beams of light may be directed to the specimen substantially simultaneously or sequentially.

The inspection system of FIG. 1 includes a single collection channel. For example, light scattered from the specimen may be collected by collector 16, which may be a lens, a compound lens, or any appropriate lens known in the art. Alternatively, collector 16 may be a reflective or partially reflective optical component, such as a mirror. In addition, although one particular collection angle is illustrated in FIG. 1, it is to be understood that the collection channel may be arranged at any appropriate collection angle. The collection angle may vary depending upon, for example, the angle of incidence and/or topographical characteristics of the specimen.

The inspection system also includes a detector 18 for detecting the light scattered from the specimen and collected by collector 16. Detector 18 generally functions to convert the scattered light into an electrical signal, and therefore, may include substantially any photodetector known in the art. However, a particular detector may be selected for use within one or more embodiments of the invention based on desired performance characteristics of the detector, the type of specimen to be inspected and/or the configuration of the illumination subsystem. For example, if the amount of light available for inspection is relatively low, an efficiency enhancing detector such as a time delay integration (TDI) camera may increase the signal-to-noise ratio and throughput of the system. However, other detectors such as charge-coupled device (CCD) cameras, photodiodes, phototubes and photomultiplier tubes (PMTS) may be used, depending on the amount of light available for inspection and the type of inspection being performed. In at least one embodiment of the invention, a photomultiplier tube is used for detecting light scattered from a specimen.

The inspection system also includes various electronic components needed for processing the scattered signals detected by detector 18. For example, the system shown in FIG. 1 includes amplifier circuitry 20, analog-to-digital converter (ADC) 22 and processor 24. Amplifier 20 is generally configured to receive output signals from detector 18 and to amplify those output signals by a predetermined amount. ADC 22 converts the amplified signals into a digital format suitable for use within processor 24. In one embodiment, the processor may be coupled directly to ADC 22 by a transmission medium, as shown in FIG. 1. Alternatively, the processor may receive signals from other electronic components coupled to ADC 22. In this manner, the processor may be indirectly coupled to ADC 22 by a transmission medium and any intervening electronic components.

In general, processor 24 is configured for detecting features, defects, or light scattering properties of the specimen using electrical signals obtained from the single collection channel. The signals produced by the single collection channel are representative of the light detected by a single detector (detector 18). The term "single detector" may be used herein to describe a detector having only one sensing area, or possibly several sensing areas (such as found, e.g., in a detector array or multi-anode PMT). Regardless of number, the sensing areas of a single detector are embodied within a single enclosure. In some cases, the inspection system described herein may be used for inspecting patterned, as well as unpatterned specimens. The processor may include any appropriate processor known in the art. In addition, the processor may be configured to use any appropriate defect detection algorithm or method known in the art. For example, the processor may use a die-to-database comparison or a thresholding algorithm to detect defects on the specimen.

The inspection system described herein provides more features, defects, or light scattering property information about specimens than other inspection systems, which trade-off detection range for sensitivity (or vice versa). In other words, the inspection system described herein provides extended detection range (e.g., about 0 to about 3 orders of magnitude, or more) without sacrificing sensitivity. The improved inspection system also maintains excellent signal linearity and stability, and does not require complex calibrations or additional detectors and optics to extend the detection range. The improved inspection system achieves all this by addressing several factors, which tend to limit the detection range of an inspection system. These factors include, but are not limited to, detector saturation, amplifier saturation and the fixed bit range of analog-to-digital converters. The limitations set by detector saturation will now be described in the context of photomultiplier tubes. It is recognized, however, that the general concepts outlined below may be applicable to other types of detectors.

Photomultiplier tubes (PMTS) are often used as detectors when optical signals are dim (i.e., in low-intensity applications, such as fluorescence spectroscopy). A typical photomultiplier tube consists of a photoemissive cathode (photocathode) followed by focusing electrodes, a plurality of dynodes (forming an electron multiplier) and an anode (forming an electron collector) in a vacuum tube. When light enters the PMT, the photocathode emits photoelectrons into the vacuum. The focusing electrodes direct the photoelectrons towards the electron multiplier where electrons are multiplied by the process of secondary emission. For example, the photoelectrons are accelerated from the photocathode to the first dynode by an electric field. When they strike the dynode, they dislodge additional electrons to amplify the photoelectric signal. These secondary electrons cascade towards the next dynode where they are again amplified. At the end of the dynode chain, the electrons are collected by the anode to generate an electrical output signal in proportion to the amount of light entering the PMT. The output signal produced at the anode is generally large enough to be measured using conventional electronics, such as a transimpedance amplifier followed by an analog-to-digital converter.

The process of secondary emission enables the photomultiplier tube to achieve high current amplification. In other words, a very small photoelectric current from the photocathode can be observed as a large output current from the anode of the photomultiplier tube. Current amplification (otherwise referred to as gain) is simply the ratio of the anode output current to the photoelectric current from the photocathode. The gain at each dynode is a function of the energy of the incoming electrons, which is proportional to the electric potential between that dynode and the previous stage. The total gain of the PMT is the product of the gains from all of the dynode stages. When a voltage (V) is applied between the cathode and the anode of a photomultiplier tube having (n) dynode stages, the total gain becomes: $G(V)$ varies $V^{\alpha \cdot n}$ EQ. 1 where, $\alpha$ is a coefficient determined by the dynode material and geometric structure (typically in the range of 0.6 to 0.8).

In most cases, a photomultiplier tube will be operated at a single predetermined gain. For example, bias voltages may be generated for each of the dynodes by connecting a string of voltage-divider resistors between the cathode, all of the dynodes, the anode and ground. The resistance, R, is used as a scaling constant and is typically the same for all stages of the photomultiplier tube. A large negative voltage (typically −500 V to −1500 V) is then applied to the cathode, and the potential is divided up evenly across the dynodes by the voltage-divider resistor chain. Doing so enables each of the dynodes to be maintained at successively less negative potentials, the difference between which establishes the intermediate dynode gain. Though the total gain of the photomultiplier tube may be altered by changing the voltage applied to the cathode, it is generally not desirable to do so. For example, the large voltages involved make it difficult to change the gain quickly, due to parasitic capacitances and the large resistor values needed to limit power dissipation in the bias string. Therefore, most users decide on a tube gain in advance, set the appropriate cathode voltage and then operate the tube at that voltage throughout the measurement operations.

In this configuration, the detection range of the photomultiplier tube is limited on the low end by the noise and gain characteristics of the transimpedance amplifier and, on the high end, by the ability of the photomultiplier tube to deliver anode current. In low-intensity applications, the anode current is limited by space charge effects within the tube, bias string power consumption, and the consumable nature of the material coating the dynodes. In high-intensity applications, the photomultiplier tube is limited by saturation of the anode, and sometimes, the cathode. For example, the photomultiplier tube may provide inaccurate results when relatively large amounts of light cause the anode (or cathode) to become saturated. In the following embodiments, the present invention addresses anode saturation as a limiting factor to the detection range of an inspection system. As described in more detail below, the present invention avoids measurement inaccuracies and extends the detection range of a PMT detector by providing circuits and methods designed, in one aspect, for avoiding anode saturation.

Additional embodiments of inspection systems in which the subject matter described herein may find utility are described in U.S. Pat. Nos. 6,538,730, 6,271,916, 6,201,601, 6,956,660, 7,218,391, and 7,061,601, the disclosures of which are incorporated herein by reference in their entirety. These inspections systems generally operate by mounting an object on a rotatable spindle assembly, which in turn comprises a chuck on which the object may be mounted. A first drive assembly rotates the spindle about a central axis, such that the first radiation beam and the second radiation beam scan a portion of the surface of the object, while a second drive assembly induces radial motion between the optical assembly and the object being inspected, such that a radiation beam is scanned across the surface of the object. In alternate embodiments, an inspection system may implement an X-Y scanning pattern to scan the surface of the object.

Figure 2:
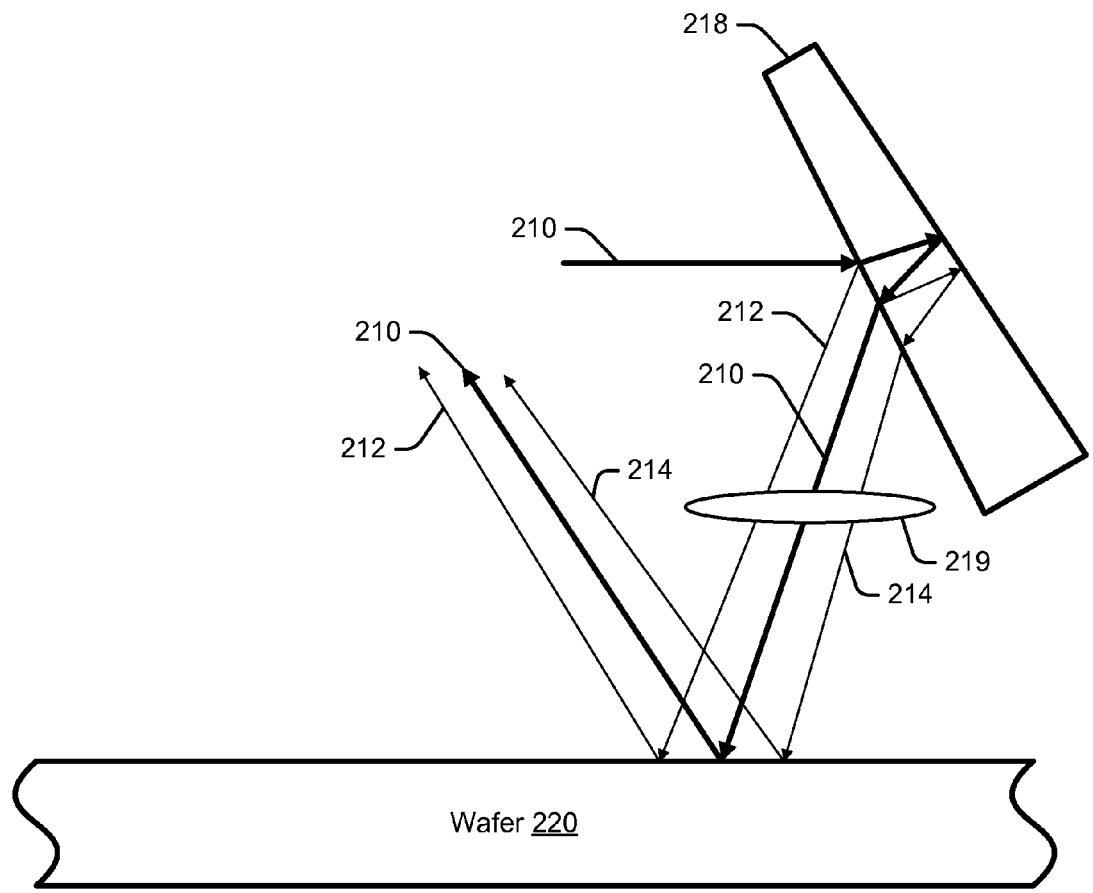
FIG. 2 is a schematic illustration of an embodiment of a mirror to generate secondary beams from a primary beam.

In some embodiments, the inspection system may be adapted to provide a radiation targeting assembly which targets a first radiation beam and a second radiation beam onto a first surface of the object in close physical proximity. The first radiation beam impinges the first surface at a first intensity and the second radiation beam impinges the first surface proximate the first beam and at a second intensity, greater than the first intensity. In some environments, the second beam represents the primary been used for scanning the surface, while the first beam is a secondary, or phantom, beam which may be used to implement a dynamic range extension routine, alone or in combination with a power attenuation routine. FIG. 2 is a schematic illustration of an embodiment of an arrangement to generate secondary beams from a primary beam. In one embodiment, a wedged folded mirror in the optical path between the first radiation source and the first surface, such that a first portion of a radiation beam from the radiation source reflects from a front surface of the mirror and a second portion of the radiation beam from the radiation source reflects from a rear surface of the mirror.

Referring to FIG. 2, in one embodiment, a mirror 218 is positioned in the optical path between a radiation source and the surface of the object. In some embodiments, mirror 218 is a folding mirror in which the front surface and rear surface are non-parallel, The radiation beam 210 from the radiation source impinges the front surface of the mirror 218. A small portion of the radiation incident on the front surface of the near 218 is reflected first from the front surface of the mirror 218 and then from the surface of wafer 220, as indicated by ray 212. By contrast, a major portion of the radiation 210 incident on the surface of mirror 218 is transmitted across the front surface of the mirror 218 and reflected by the rear surface of the mirror 218 onto the surface of the wafer 220, which in turn reflects the radiation, as indicated by ray 210. A further minor portion of the radiation reflected from the rear surface of mirror 218 is internally reflected at the front surface of the mirror 218. This portion of the radiation reflects a second time from the rear surface of the mirror 218 onto the surface of wafer 220, which reflects the radiation as indicated by ray 214.

Because the front and rear surfaces of mirror 218 are non-parallel, the scattered light beams 212 and 214 diverge from the light beam 210, as illustrated in FIG. 2. A spot forming lens 219 on the incident side of the system may be implemented to produce an offset distance on the wafer as a function of the focal length of the lens and the angle between the beams 210, 212, 214. In order to prevent the lateral offset (shear) from requiring the downstream optics to be much larger than the dimensions of either the primary or secondary beams, the incidence angles should be small especially if the thickness of the wedge is large (to maintain good surface flatness, i.e. wavefront quality) but not so small as to require an extremely long distance to separate the incoming and outgoing beams. For example, the incident angle of the incoming radiation onto the wedge should be between 3 and 5 degrees.

Thus, the imposition of mirror 218 into the optical path of radiation 210 generates a radiation beam suitable for use as a primary scanning radiation beam 210 and two beams suitable for use as secondary beams, represented by beams 212 and 214. In some embodiments the primary beam 210 maintains between ninety percent and 99.9 percent of the intensity of the incident radiation, while the remaining intensity is split between the secondary beams 212 and 214. The amount of energy maintained in the primary beam is a function of the index of refraction and the efficiency of reflection of the material from which mirror 218 is formed, and of the incident angle of the radiation beam 210. In some embodiments, the mirror 218 is positioned such that the radiation strikes the surface of the mirror 218 at an incidence angle that measures between preferably 3 degrees and 5 degrees, but in general could be at any angle between 0 degrees and 45 degrees. Thus, the mirror 218 provides a low intensity secondary beam 212 that leads the primary beam 210 on the surface of the wafer 220. The mirror 218 further provides a low intensity secondary beam 214 that follows the primary beam 210 on the surface of wafer 220. In some embodiments, secondary beam 214 is not used for any practical processing and may be blocked or simply ignored. Also, depending upon the material from which mirror 218 is formed, the primary and secondary beams may have the same polarization or may have different polarizations.

The distance by which primary and secondary beams are separated on the surface of wafer 220 may be a function of the defect size to be analyzed by the system, i.e., the distance between the beams may be selected such that the largest feature to be detected still generates separable signals. For example, if particles up to 10 micrometers (um) are to be detected and the beam with is 10 um (1/e^2), the primary and secondary beams should be separated by approximately 50 um, thereby providing 20 um around each beam for the beam tails and 10 um separation between so the particle will not be seen by both beams at the same time.

Figure 3:
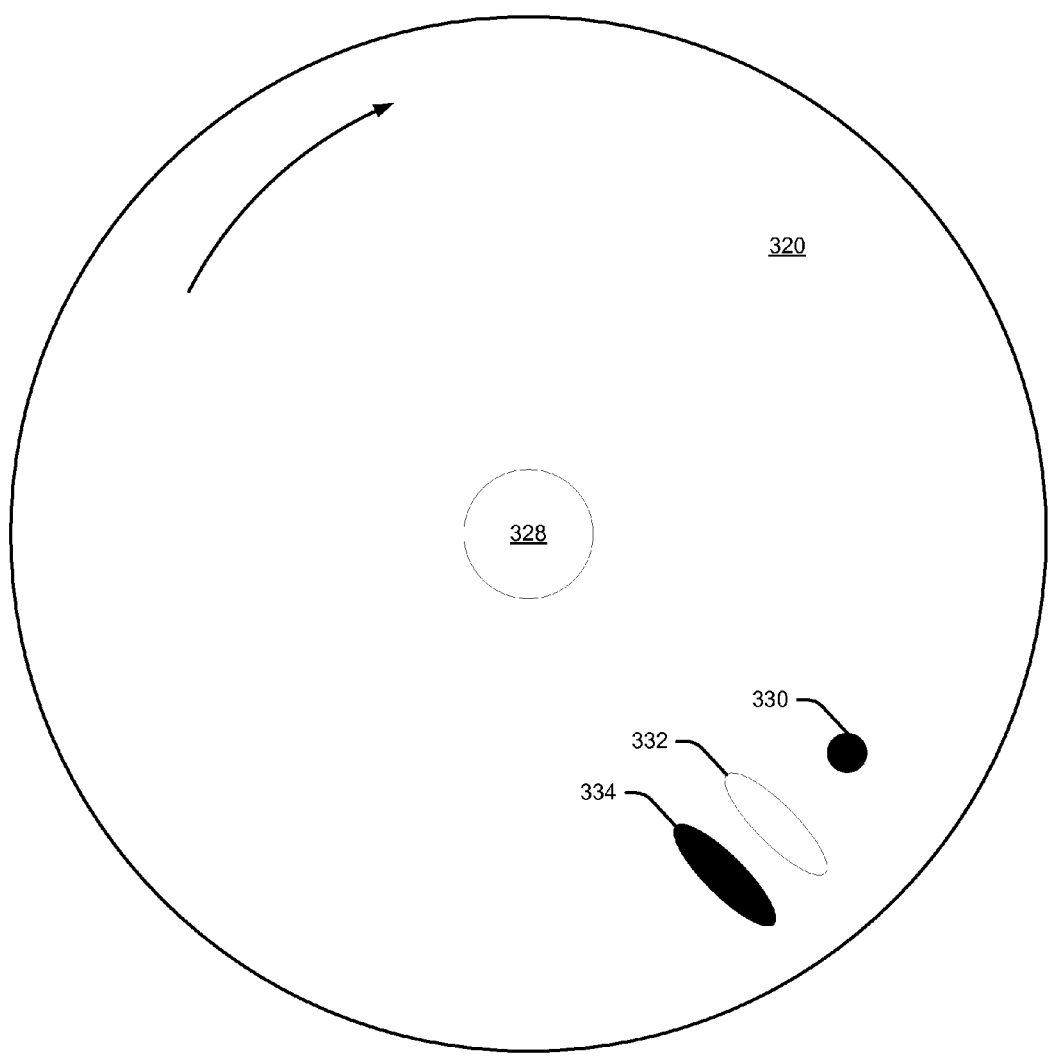
FIG. 3 is a schematic illustration of a beam configuration in scan operations, according to embodiments.

FIG. 3 is a schematic illustration of a beam configuration in scan operations, according to embodiments. Referring to FIG. 3, in operation the spindle assembly 328 rotates the wafer 320 about a central axis such that radiation from the radiation targeting assembly scans the surface of the wafer 320. In the embodiment depicted in FIG. 3, the wafer 320 rotates clockwise as indicated by the arrow. The radiation targeting assembly generates a first radiation beam 332 and a second radiation beam 334 on the surface of the wafer 320. The radiation beam 334 represents the primary scanning radiation beam and the radiation beam 332 represents the secondary radiation beam. When the beams 332, 334 are incident upon a defect 330 on the surface of wafer 320, the reflection from each beam 332, 334 is incident on the detectors 140, 142 which generate a signal corresponding to each reflection. Thus, each defect detected on the surface of wafer 320 generates two data points in sets of data collected from the surface of wafer 320.

Figure 4A:
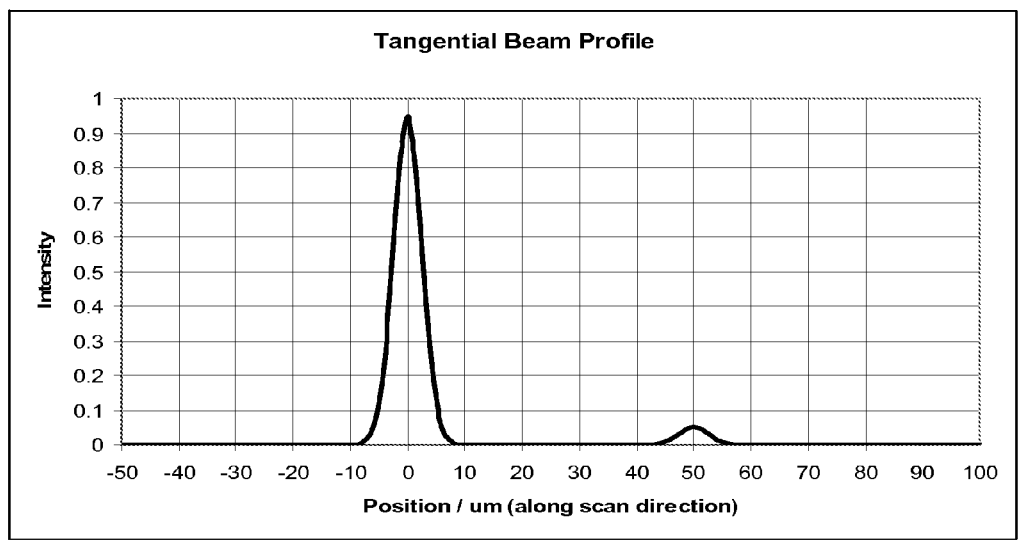
FIG. 4a is a schematic illustration of intensity profiles of primary and secondary beams, according to embodiments.

As described above, the secondary beam is significantly less intense than the primary beam. Therefore, the signal generated in response to the reflection from the secondary beam will be significantly lower than the signal generated in response to the primary beam. This is illustrated with reference to FIG. 4A, which is a schematic illustration of intensity profiles of primary and secondary beams, according to embodiments. In the embodiment depicted in FIG. 4A the primary and secondary beams are separated by distance of approximately 50 micrometers. When the beams encounter a defect on the surface a small signal is generated by the secondary beam which is offset from the large signal generated by the primary beam by approximately 50 micrometers.

Figure 4B:
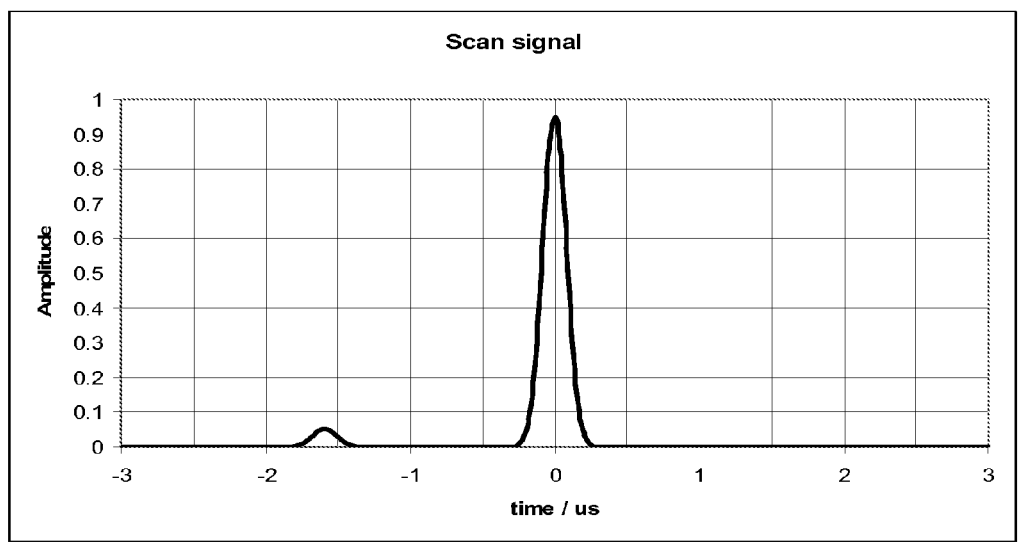
FIG. 4b is a schematic illustration of signal amplitudes of primary and secondary beams, according to embodiments.

FIG. 4B is a schematic illustration of signal amplitudes of primary and secondary beams, according to embodiments, on a scale which has been transformed from distance to time, assuming a scan speed of approximately thirty one (31) meters per second. The signal generated by the secondary beam is separated from the signal generated by the primary beam by approximately 1.6 microseconds (us).

Figure 5:
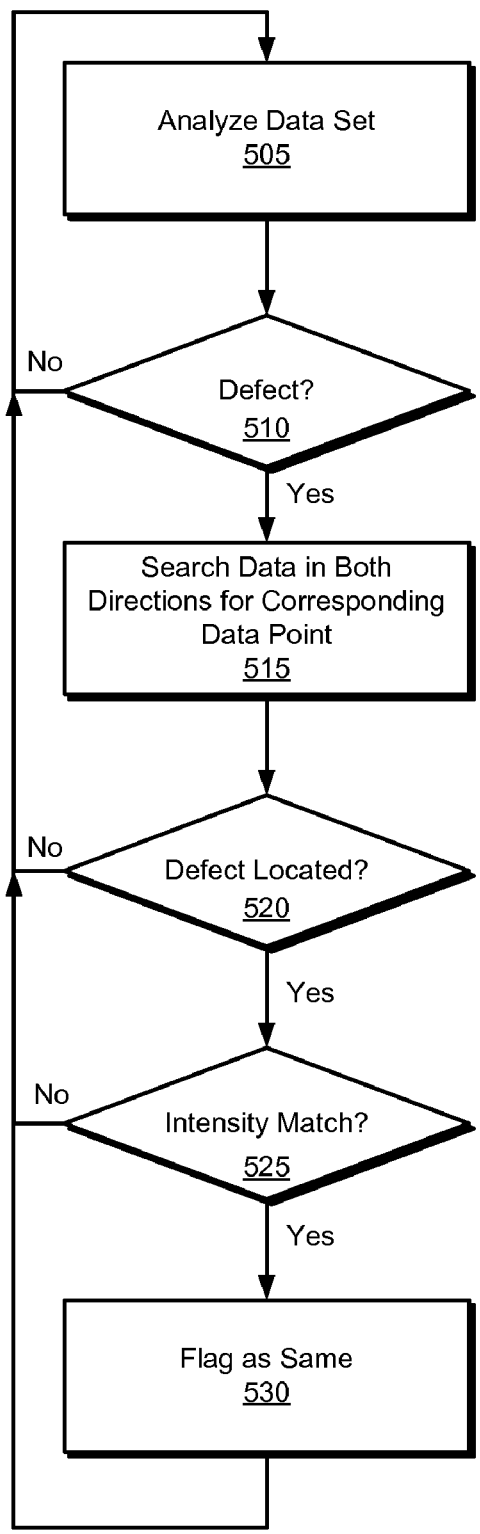
FIG. 5 is a flowchart illustrating operations in an embodiment of a method to correlate points in a data set, according to embodiments.

In some embodiments, the data processing module 170 implements a routine to associate data points resulting from the same defect in the data set generated by a scan of the surface of a wafer. For example, as illustrated above the primary beam in the secondary beam will each generate distinct data points in the data set for each defect on the surface. FIG. 5 is a flowchart illustrating operations in an embodiment of a method to correlate points in a data set, according to embodiments. In general, for each detected defect signal, the first task is to find if it is originating from the main beam or from the secondary beam. This may be accomplished by searching at the pre-determined separation in both directions. If another defect signal is found within the expected distance range and the intensity ratio matches the pre-determined actual ratio of the beam intensities, both defect signals will be flagged as belonging to the same defect.

More specifically, referring to FIG. 5, at operation 505 the data processing module initiates an analysis of the data set collected by scanning the surface of an object such as a wafer. When a defect is located at operation 510 the data in the data set is searched in both a forward direction and a backward direction for data points corresponding to the distance of separation between the primary beam in the secondary beam on the surface. If, at operation 520, no defect is located then control passes back to operation 505 and the analysis continues. By contrast, when a defect is located at operation 520 control passes to operation 525 where it is determined whether there is an intensity match between the defect data. For example, if the radiation from the radiation source is divided into a primary beam which contains approximately 99% of the intensity of the original beam and the secondary beam contains approximately 1% of the intensity of the original beam, and if the response curve of the detectors 140, 142 is substantially linear within the operating range of the signals generated by the system then the defect data point generated by the primary beam should be approximately 99 times the defect data generated by the secondary beam. In practice an approximation routine may be implemented in which a threshold is set around the expected relationship between the primary and secondary data sets. If the intensity of the two beams falls within the threshold than the two data points may be considered as resulting from the primary beam and the secondary beam being incident upon the same defect so control passes to operation 530 in the data points are flagged as being from the same defect. The larger data point would be flagged as resulting from the primary beam and the smaller data point would be flagged as resulting from the secondary beam. Control then passes back to operation 505 and the analysis routine continues.

In normal operation, the data points generated by the secondary beam may be ignored during data processing operations for determining defects on the surface of the object being analyzed. However, in some instances large defects may generate signals of intensity sufficient to overload the detectors 140, 142. Therefore, in some embodiments, once the data set has been analyzed such that data points from the primary beam and the secondary beam have been associated the data processing module 170 may implement a dynamic range extension routine. For example, the dynamic range extension routine may be utilized when a data point in the first data set exceeds a threshold that corresponds to the saturation point, or upper limit, of the detectors 140, 142.

Figure 6:
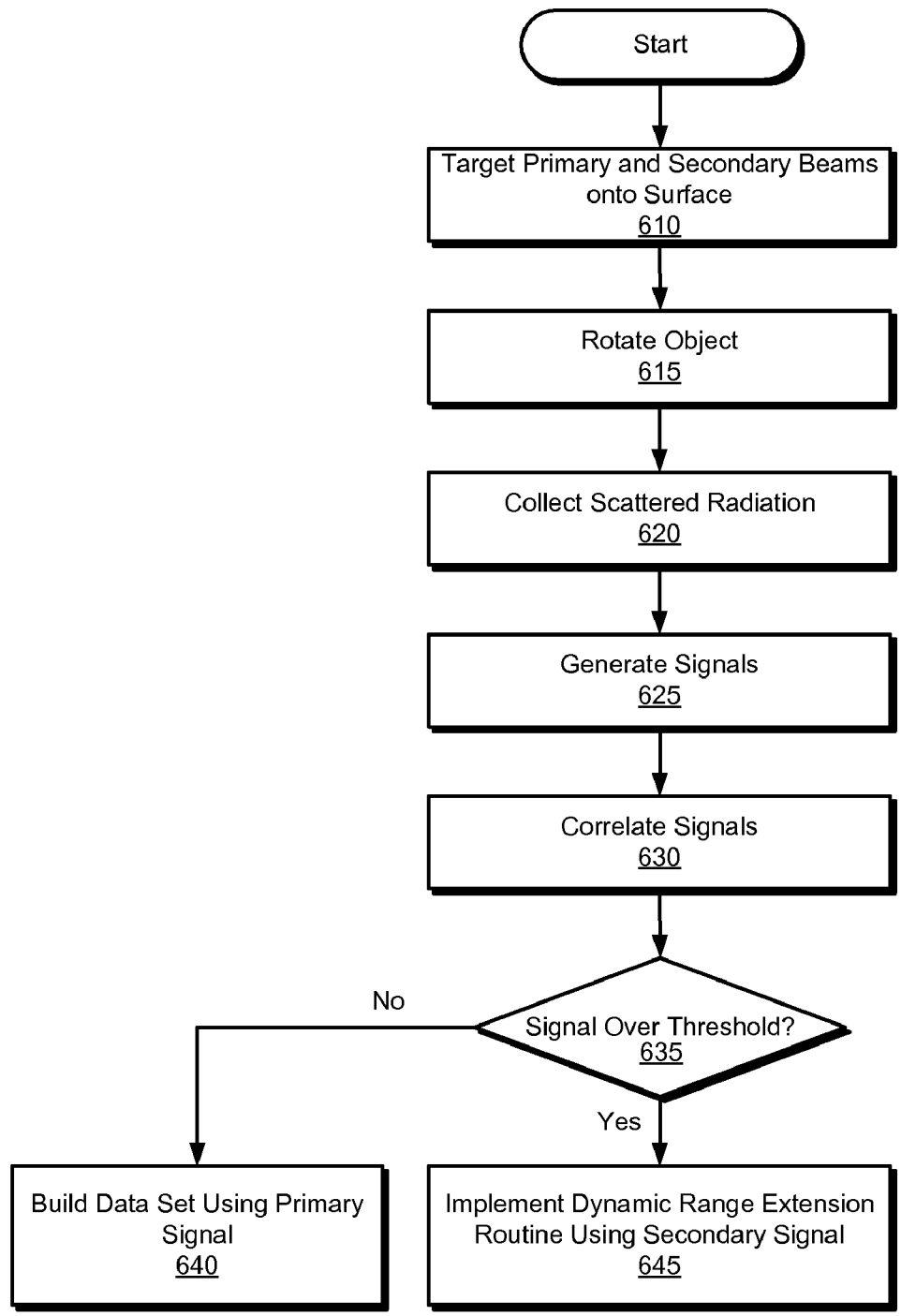
FIG. 6 is a flowchart illustrating operations in an embodiment of a method for dynamic range extension in surface inspection systems, according to embodiments.

FIG. 6 is a flowchart illustrating operations in an embodiment of a method for dynamic range extension in surface inspection systems, according to embodiments. Referring to FIG. 6, at operation 610 primary and secondary beams are targeted onto the surface of the object being scanned. For example the primary and secondary beams may correspond to primary and secondary beams as described above. At operation 615 the object is rotated about a central axis. For example, the object may be positioned on a rotating spindle as described above. At operation 620 radiation from the primary and secondary beams that is scattered from the surface of the object is collected, and at operation 625 signals are generated from the scattered radiation. Operation 630 the signals are correlated. For example, the signal could be correlated these in the operations described with reference to FIG. 5 to establish a logical association between data points generated from signals from the primary beam and signals from the secondary beam. If, at operation 635, the signals in the data set do not exceed the threshold and the entire data set may be built using data collected from the primary signal.

If, at operation 635 a data point indicates that a signal exceeds a threshold, then control passes to operation 645 and a dynamic range extension routine is implemented. In one embodiment, the dynamic range extension routine locates a second data point in the data set which was generated by the same defect as the first defect and multiplies the value of the second data point by the intensity ratios of the first radiation beam and the second radiation beam. For example, in practice signal thresholds will be exceeded by the primary beam, not by the secondary beam. When a data point in the data set is encountered that exceeds a threshold, the data processing module retrieves the data point in the data set for the same defect that was generated by the secondary beam. The data point resulting from the secondary beam may then be multiplied by the intensity ratio of the primary beam to the secondary beam, and the resulting value may be used to replace the data point that exceeded the threshold. Again, suitable adjustments to this calculation may be necessary if the detectors 140, 142 are not operating within a linear response range. Such adjustments are within the skill of one having ordinary skill in the art.

In another embodiment, the primary and secondary radiation beams may be used to implement a power attenuation procedure, alone or in combination with the dynamic range extension procedure described herein. For example, the system may implement a real-time laser power attenuation, which may be used to avoid damage to the detectors 140, 142 are other components of the system caused by excessive reflection of beam intensity in the primary beam.

Figure 7:
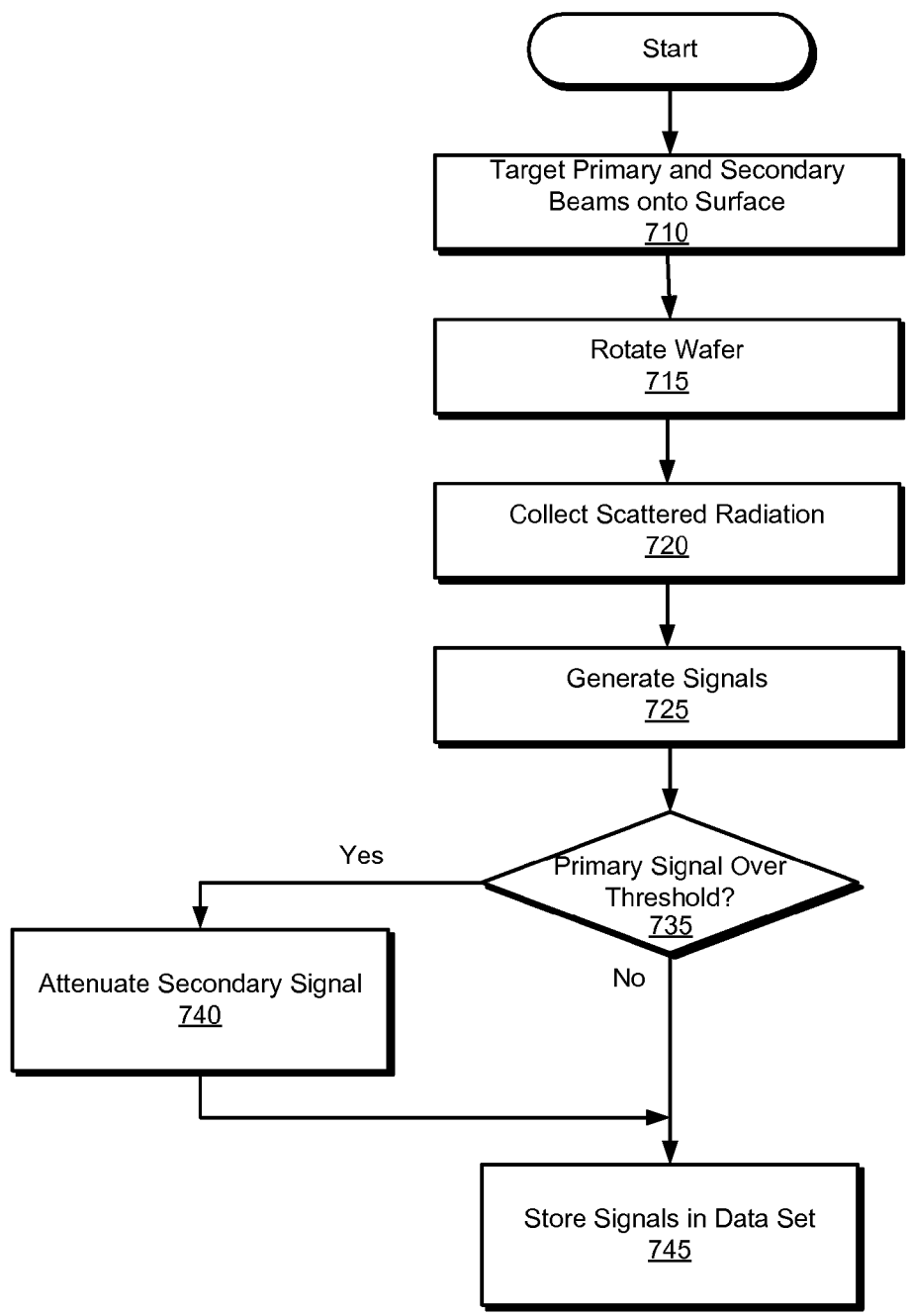
FIG. 7 is a flowchart illustrating operations in an embodiment of a method for selective signal attenuation in surface inspection systems, according to embodiments.

FIG. 7 is a flowchart illustrating operations in an embodiment of a method for selective signal attenuation in surface inspection systems, according to embodiments. Referring to FIG. 7, at operation 710 primary and secondary beams are targeted onto the surface of the object being scanned. For example the primary and secondary beams may correspond to primary and secondary beams as described above. At operation 715 the object is rotated about a central axis. For example, the object may be positioned on a rotating spindle as described above. At operation 720 radiation from the primary and secondary beams that is scattered from the surface of the object is collected, and at operation 725 signals are generated from the scattered radiation. If, at operation 735, the signals in the data set do not exceed the threshold then control passes to operation 745 in the signals generated may be stored in the data set.

If, at operation 735 the primary signal exceeds a threshold, then control passes to operation 740 and the secondary signal is attenuated to avoid generating an excessively strong signal in the system. In one embodiment, the primary signal may be attenuated by reducing the output power of the laser by a predetermined amount, with a fast laser power attenuator. In alternate embodiments, the primary signal may be attenuated by filtering a predetermined portion of the radiation in the primary beam. Control then passes to operation 745 and the signal resulting from the attenuated primary beam is stored in the data set. In one embodiment, and attenuation factor may be stored in logical association with the data point where data points generated by reflections from the attenuated primary beam. The data points resulting from the attenuated primary signal may be multiplied by the inverse of the attenuation factor to normalize the data. For example, if the attenuation routine applies and attenuation factor of 0.5, the resulting data may be multiplied by two to normalize the data. Again, this normalization routine assumes that the detectors 141, 142 are operating within a linear response range. Adjustments may be required if the response of detectors 140, 142 is not linear.

Thus, described herein are systems and methods which utilize a primary and a secondary beam to implement dynamic range extension, alone or in combination with power attenuation techniques, to permit the system to compensate for situations in which reflections from a primary beam exceed operational thresholds of components of the system. This permits inspection systems to operate at higher power ranges, which enhances the ability of the system to detect defects.

Reference in the specification to "one embodiment" or "an embodiment" means that a particular feature, structure, or characteristic described in connection with the embodiment is included in at least an implementation. The appearances of the phrase "in one embodiment" in various places in the specification may or may not be all referring to the same embodiment.

Thus, although embodiments have been described in language specific to structural features and/or methodological acts, it is to be understood that claimed subject matter may not be limited to the specific features or acts described. Rather, the specific features and acts are disclosed as sample forms of implementing the claimed subject matter.

What is claimed is:

1. A system to analyze a surface of an object, comprising:
a first radiation source;
a radiation targeting assembly to scan a first radiation beam from the first radiation source across a portion of a first surface of the object, wherein the first radiation beam impinges the first surface at a first intensity and a to scan a second radiation beam across a portion of the first surface of the object, wherein the second radiation beam impinges the first surface proximate the first beam and at a second intensity, greater than the first intensity;
a scattered radiation collecting assembly to collect portions of a first scattered radiation beam scattered from the first surface, wherein the first scattered radiation beam results from a reflection of the first radiation beam, and to collect portions of a second scattered radiation beam scattered from the first surface, wherein the second scattered radiation beam results from a reflection of the second radiation beam;
a detector assembly coupled to the scattered radiation collecting assembly to generate a first signal from the first scattered radiation beam rand a second signal from the second scattered radiation beam;
a signal processing module to generate a data set from the first signal and the second signal as the first radiation beam and the second radiation beam scan a portion of the surface of the object; and
a data processing module to use data in the data set to evaluate defects in the surface of the object.

2. The system of claim 1, wherein the radiation targeting assembly comprises a wedged folded mirror in the optical path between the first radiation source and the first surface, such that a first portion of a radiation beam from the radiation source reflects from a front surface of the minor and a second portion of the radiation beam from the radiation source reflects from a rear surface of the minor.

3. The system of claim 2, wherein a third portion of the radiation beam from the radiation source is internally reflected at the front surface of the reflected minor and reflects from the rear surface of the mirror.

4. The system of claim 2, wherein the first portion of the radiation beam reflected from the minor corresponds to the first radiation beam and the second portion of the radiation beam reflected from the mirror corresponds to the second radiation beam.

5. The system of claim 4, wherein the intensity of the first radiation beam is less than ten percent of the intensity of the second radiation beam.

6. The system of claim 1, wherein the first radiation beam and the second radiation beam are incident on the surface at location separated by less than 100 micrometers.

7. The system of claim 1, wherein the data processing module:
analyzes the data set to locate data points in the data set that were generated by the same defect in the surface.

8. The system of claim 7, wherein the data processing module implements a dynamic range extension routine when a first data point in the data set exceeds a threshold.

9. The system of claim 8, wherein the dynamic range extension routine:
locates a second data point in the data set which was generated by the same defect as the first defect; and
multiplies the value of the second data point by the intensity ratios of the first radiation beam and the second radiation beam.

10. The system of claim 1, further comprising a power attenuation module, which:
compares the first signal from the first scattered beam to a threshold; and
attenuates the second radiation beam when signal from the first scattered beam exceeds the threshold.

11. A method to analyze a surface of an object, comprising:
scanning a first radiation beam from the first radiation source across a portion of a first surface of the object, wherein the first radiation beam impinges the first surface at a first intensity, and scanning a second radiation beam across a portion of the first surface of the object, wherein the second radiation beam impinges the first surface proximate the first beam and at a second intensity, greater than the first intensity;
collecting portions of a first scattered radiation beam scattered from the first surface, wherein the first scattered radiation beam results from a reflection of the first radiation beam, and portions of a second scattered radiation beam scattered from the first surface, wherein the second scattered radiation beam results from a reflection of the second radiation beam;
generating a first signal from the first scattered radiation beam and a second signal from the second scattered radiation beam;
generating a data set from the first signal and the second signal as the first radiation beam and the second radiation beam scan a portion of the surface of the object; and
using data in the data set to evaluate defects in the surface of the object.

12. The method of claim 11, further comprising positioning a wedged folded minor in the optical path between the first radiation source and the first surface, such that a first portion of a radiation beam from the radiation source reflects from a front surface of the minor and a second portion of the radiation beam from the radiation source reflects from a rear surface of the mirror.

13. The method of claim 12, wherein a third portion of the radiation beam from the radiation source is internally reflected at the front surface of the reflected minor and reflects from the rear surface of the mirror.

14. The method of claim 12, wherein the first portion of the radiation beam reflected from the minor corresponds to the first radiation beam and the second portion of the radiation beam reflected from the mirror corresponds to the second radiation beam.

15. The method of claim 14, wherein the intensity of the first radiation beam is less than ten percent of the intensity of the second radiation beam.

16. The method of claim 15, wherein the first radiation beam and the second radiation beam are incident on the surface at location separated by less than 100 micrometers.

17. The method of claim 11, further comprising analyzing the data set to locate data points in the data set that were generated by the same defect in the surface.

18. The method of claim 17, further comprising implementing a dynamic range extension routine when a first data point in the data set exceeds a threshold.

19. The method of claim 18, further comprising:
locating a second data point in the data set which was generated by the same defect as the first defect; and
multiplying the value of the second data point by the intensity ratios of the first radiation beam and the second radiation beam.

20. The system of claim 1, further comprising a power attenuation module, which:
comparing the first signal from the first scattered beam to a threshold; and
attenuating the second radiation beam when signal from the first scattered beam exceeds the threshold.

21. A system to analyze a surface of an object, comprising:
a first radiation source;
a radiation targeting assembly to scan a first radiation beam from the first radiation source across a portion of a first surface of the object, wherein the first radiation beam impinges the first surface at a first intensity and to scan a second radiation beam across a portion of the first surface of the object, wherein the second radiation beam impinges the first surface proximate the first beam and at a second intensity, greater than the first intensity;
a scattered radiation collecting assembly to collect portions of a first scattered radiation beam scattered from the first surface, wherein the first scattered radiation beam results from a reflection of the first radiation beam, and to collect portions of a second scattered radiation beam scattered from the first surface, wherein the second scattered radiation beam results from a reflection of the second radiation beam;
a detector assembly coupled to the scattered radiation collecting assembly to generate a first signal from the first scattered radiation beam rand a second signal from the second scattered radiation beam; and
a power attenuation module, which:
compares the first signal from the first scattered beam to a threshold; and
attenuates the second radiation beam when signal from the first scattered beam exceeds the threshold.

22. The system of claim 1, wherein the radiation targeting assembly comprises a wedged folded mirror in the optical path between the first radiation source and the first surface, such that a first portion of a radiation beam from the radiation source reflects from a front surface of the minor and a second portion of the radiation beam from the radiation source reflects from a rear surface of the minor.

23. The system of claim 21, wherein the intensity of the first radiation beam is less than ten percent of the intensity of the second radiation beam.

24. The system of claim 21, further comprising:
a signal processing module to generate a data set from the first signal and the second signal as the first radiation beam and the second radiation beam scan a portion of the surface of the object; and
a data processing module to use data in the data set to evaluate defects in the surface of the object, wherein the data processing module analyzes the data set to locate data points in the data set that were generated by the same defect in the surface.

25. The system of claim 24, wherein the data processing module implements a dynamic range extension routine when a first data point in the data set exceeds a threshold.

26. The system of claim 25, wherein the dynamic range extension routine:
locates a second data point in the data set which was generated by the same defect as the first defect; and
multiplies the value of the second data point by the intensity ratios of the first radiation beam and the second radiation beam.

* * * * *